US011875617B2

(12) United States Patent
Ventimiglia et al.

(10) Patent No.: US 11,875,617 B2
(45) Date of Patent: Jan. 16, 2024

(54) CLOUD CONNECTIVITY FOR IN-VEHICLE SENSING MODULES

(71) Applicant: Robert Bosch GmbH, Stuttgart (DE)

(72) Inventors: Philip Ventimiglia, Northville, MI (US); Krisztian Bakos, Redondo Beach, CA (US); Karl Holodnick, Northville, MI (US); Russell Watts, Ann Arbor, MI (US); George Lewis, Brighton, MI (US); Stefan Weissert, Royal Oak, MI (US)

(73) Assignee: Robert Bosch GmbH, Stuttgart (DE)

( * ) Notice: Subject to any disclaimer, the term of this patent is extended or adjusted under 35 U.S.C. 154(b) by 326 days.

(21) Appl. No.: 17/116,142

(22) Filed: Dec. 9, 2020

(65) Prior Publication Data
US 2021/0194960 A1    Jun. 24, 2021

Related U.S. Application Data

(60) Provisional application No. 62/952,623, filed on Dec. 23, 2019, provisional application No. 62/952,568, (Continued)

(51) Int. Cl.
*G07C 5/08* (2006.01)
*G07C 5/02* (2006.01)
(Continued)

(52) U.S. Cl.
CPC ......... *G07C 5/085* (2013.01); *G01C 21/3438* (2013.01); *G01C 21/3484* (2013.01); *G01N 33/0031* (2013.01); *G01N 33/0047* (2013.01); *G01P 15/14* (2013.01); *G01S 19/13* (2013.01); *G01V 8/10* (2013.01); *G06V 20/59* (2022.01);
(Continued)

(58) Field of Classification Search
CPC .......... G07C 5/085; G07C 5/008; G07C 5/02; B60W 60/001; G06V 20/59; G01C 21/3438; G01C 21/3484; G01N 33/0047; G01P 15/14; G01S 19/13; G01V 8/10;
(Continued)

(56) References Cited

U.S. PATENT DOCUMENTS

| 3,954,204 A | 5/1976 | Becker et al. |
| 9,602,779 B2 | 3/2017 | DeJuliis |

(Continued)

FOREIGN PATENT DOCUMENTS

| WO | WO-2019152471 A2 * | 8/2019 | ............. G06F 21/36 |
| WO | WO-2019180700 A1 * | 9/2019 | ............. B60W 30/16 |

*Primary Examiner* — John A Follansbee
*Assistant Examiner* — Raqiul A Choudhury
(74) *Attorney, Agent, or Firm* — Maginot, Moore & Beck LLP

(57) ABSTRACT

A cloud storage backend for managing data of in-vehicle sensing modules is disclosed, which is advantageous for use in the context of a shared vehicle service, such as a car rental service, an autonomous taxi service, or a ride sharing service. The in-vehicle sensing modules are configured to monitor a status of the vehicle and utilize appropriate algorithms, models, or thresholds to interpret sensor data and enrich the data with metadata and event detection. The cloud storage backend receives relevant sensor data, event data, or other metadata from the in-vehicle sensing modules and stores the data in a database which is made accessible by authorized third-parties.

18 Claims, 8 Drawing Sheets

Related U.S. Application Data filed on Dec. 23, 2019, provisional application No. 62/952,618, filed on Dec. 23, 2019.

(51) Int. Cl.

| | | |
|---|---|---|
| *G07C 5/00* | (2006.01) | |
| *H04L 12/18* | (2006.01) | |
| *H04L 67/1097* | (2022.01) | |
| *G06V 20/59* | (2022.01) | |
| *G01S 19/13* | (2010.01) | |
| *G01N 33/00* | (2006.01) | |
| *G01P 15/14* | (2013.01) | |
| *G01V 8/10* | (2006.01) | |
| *G01C 21/34* | (2006.01) | |
| *B60R 11/00* | (2006.01) | |
| *B60R 11/04* | (2006.01) | |

(52) U.S. Cl.
CPC ............... *G07C 5/008* (2013.01); *G07C 5/02* (2013.01); *H04L 12/1895* (2013.01); *H04L 67/1097* (2013.01); *B60R 11/04* (2013.01); *B60R 2011/0003* (2013.01); *B60R 2011/0026* (2013.01)

(58) Field of Classification Search
CPC . H04L 12/1895; H04L 67/1097; B60R 11/04; B60R 2011/0003
See application file for complete search history.

(56) References Cited

U.S. PATENT DOCUMENTS

| | | |
|---|---|---|
| 9,688,194 B2 | 6/2017 | MacNeille et al. |
| 10,196,070 B2 | 2/2019 | Song |
| 10,223,844 B1 | 3/2019 | Schwie et al. |
| 10,252,688 B2 | 4/2019 | Szawarski et al. |
| 10,445,950 B1 | 10/2019 | De et al. |
| 10,977,727 B1* | 4/2021 | Smith .................... G06F 16/955 |
| 11,032,372 B1* | 6/2021 | Wittevrongel .......... H04L 67/12 |
| 2015/0371456 A1 | 12/2015 | Moore, Jr. et al. |
| 2019/0197325 A1 | 6/2019 | Reiley et al. |
| 2019/0238638 A1* | 8/2019 | Way ...................... H04W 4/44 |
| 2020/0090504 A1* | 3/2020 | Kadar .................. G08G 1/0129 |
| 2020/0259919 A1* | 8/2020 | Lepp ....................... H04W 4/48 |
| 2020/0348924 A1* | 11/2020 | Park ........................ G06F 21/57 |
| 2021/0090004 A1* | 3/2021 | Smith ................ G01C 21/3438 |

\* cited by examiner

CLOUD CONNECTIVITY FOR IN-VEHICLE SENSING MODULES

CROSS-REFERENCE TO RELATED APPLICATIONS

This application claims priority to U.S. Provisional Patent Application Ser. No. 62/952,618, which is entitled "In-Vehicle Sensing Module for Monitoring a Vehicle" and was filed Dec. 23, 2019, claims priority to U.S. Provisional Patent Application Ser. No. 62/952,568, which is entitled "In-Vehicle Sensing Module for Monitoring a Vehicle" and was filed Dec. 23, 2019, and claims priority to U.S. Provisional Patent Application Ser. No. 62/952,623, which is entitled "In-Vehicle Sensing Module Having Cloud Connectivity" and was filed Dec. 23, 2019, the disclosures of which are incorporated herein by reference in their entirety.

This application is related to U.S. patent application Ser. No. 17/116,133, filed on filed on even date herewith, and to U.S. patent application Ser. No. 17/116,165, filed on even date herewith, the disclosures of which are incorporated herein by reference in their entirety.

FIELD

The device and method disclosed in this document relates to in-vehicle sensing and, more particularly, to electronic hardware for an in-vehicle sensing module.

BACKGROUND

Unless otherwise indicated herein, the materials described in this section are not admitted to be the prior art by inclusion in this section.

In shared vehicle services, such as ride sharing services, taxi services, and car rental services, shared vehicles are often driven by drivers or ridden in by passengers who are not the owner of the vehicle. A common problem with such services is that customers can be careless about how they treat the vehicle during their short time as a passenger or driver. In light of this, operators of such services often put in place various rules or policies regarding how the vehicle should be treated by the customer. However, modern incarnations of these services are technology driven and often entirely autonomous, so as to require little or no direct interaction with the owner of the vehicle or the operator of the service. As a result, effective enforcement of these rules or policies can be challenging and sometimes cost-prohibitive. Accordingly, it would be beneficial to provide a system that enables autonomous detection of issues within the vehicle that minimizes the need for human intervention in enforcing rules or policies, as well as remedying violations.

SUMMARY

A method for managing data of a vehicle monitoring system is disclosed. The vehicle monitoring system has a plurality of monitoring devices, each monitoring device of the plurality of monitoring devices being installed in a respective vehicle and having at least one sensor configured to capture respective sensor data. The method further comprises receiving, at a server, from each respective monitoring device of the plurality of monitoring devices, respective metadata indicating whether at least one predetermined condition of the respective vehicle has occurred, the respective metadata being determined by the respective monitoring device based on the respective sensor data. The method comprises storing, on a storage device connected with the server, for each respective monitoring device of the plurality of monitoring devices, the respective metadata in association with the respective monitoring device. The method further comprises providing access to the respective metadata received from each respective monitoring device of the plurality of monitoring devices, by at least one remote computing device.

A system for managing data of a vehicle monitoring system is disclosed. The system comprises a transceiver configured to communicate with a plurality of monitoring devices of the vehicle monitoring system, each monitoring device of the plurality of monitoring devices being installed in a respective vehicle and having at least one sensor configured to capture respective sensor data. The system further comprises a storage device configured to store data received from the plurality of monitoring devices. The system further comprises a processor operably connected to the transceiver and the storage device. The processor configured to operate the transceiver to receive, from each respective monitoring device of the plurality of monitoring devices, respective metadata indicating whether at least one predetermined condition of the respective vehicle has occurred, the respective metadata being determined by the respective monitoring device based on the respective sensor data. The processor further configured to operate the storage device to store, for each respective monitoring device of the plurality of monitoring devices, the respective metadata in association with the respective monitoring device. The processor further configured to operate the transceiver and the storage device to provide access to the respective metadata received from each respective monitoring device of the plurality of monitoring devices, by at least one remote computing device.

A non-transitory computer-readable medium for managing data of a vehicle monitoring system is disclosed. The vehicle monitoring system has a plurality of monitoring devices, each monitoring device of the plurality of monitoring devices being installed in a respective vehicle and having at least one sensor configured to capture respective sensor data. The computer-readable medium stores program instructions that, when executed by a processor, cause the processor to operate a transceiver to receive, from each respective monitoring device of the plurality of monitoring devices, respective metadata indicating whether at least one predetermined condition of the respective vehicle has occurred, the respective metadata being determined by the respective monitoring device based on the respective sensor data. The computer-readable medium further stores program instructions that, when executed by a processor, cause the processor to operate a storage device to store, for each respective monitoring device of the plurality of monitoring devices, the respective metadata in association with the respective monitoring device. The computer-readable medium further stores program instructions that, when executed by a processor, cause the processor to operate the transceiver and the storage device to provide access to the respective metadata received from each respective monitoring device of the plurality of monitoring devices, by at least one remote computing device.

BRIEF DESCRIPTION OF THE DRAWINGS

The foregoing aspects and other features of an in-vehicle sensing system are explained in the following description, taken in connection with the accompanying drawings.

DETAILED DESCRIPTION

Figure 1:
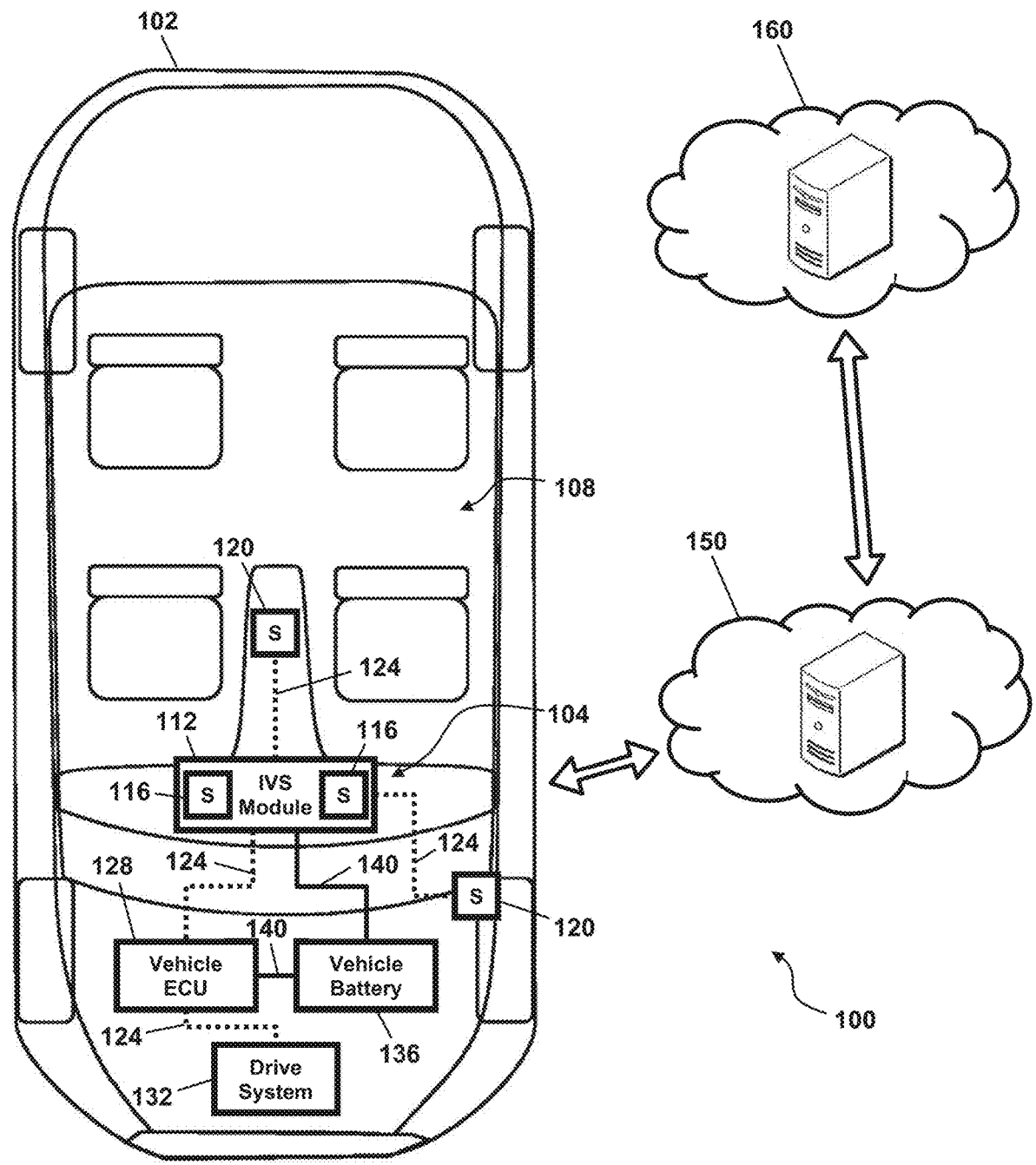
FIG. 1 shows a simplified block diagram of a vehicle monitoring system having an in-vehicle sensing module for monitoring a shared vehicle.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

System Overview

FIG. 1 shows a simplified block diagram of a vehicle monitoring system 100 having an in-vehicle sensing system 104 for monitoring at least a cabin 108 of a vehicle 102. The vehicle monitoring system 100 is advantageous for use in the context of a shared vehicle service in which the shared vehicle 102 is driven by drivers or ridden in by passengers who are not the owner of the shared vehicle 102. Such shared vehicle services might include, but are not limited to, a car rental service, an autonomous taxi service, or a ride sharing service. In many such shared vehicle services, a customer may engage the services of the shared vehicle service in an automated manner using a smartphone application, a website, an on-site kiosk, or the like, which involves little or no direct human intervention by the operator of the shared vehicle service.

The in-vehicle sensing system 104 advantageously enables operators of the shared vehicle service, to monitor the condition of the shared vehicle 102, enforce rules and policies, and provide additional benefits to the customer with minimal human intervention. Such rules and policies might include rules against smoking the shared vehicle 102 or surcharges for any required cleaning of the shared vehicle 102 after usage by the customer. Additionally, the operator can provide additional benefits to the customer, such as notifying them of left behind objects.

The in-vehicle sensing system 104 includes an in-vehicle sensing module 112 at least having a controller, a cellular transceiver/modem, and one or more integrated sensors 116 configured to monitor a status of at least the cabin 108, preferably integrated into a common housing that is installed into the cabin 108 of the vehicle. In some embodiments, the housing is configured to be mounted on a surface within the cabin 108 of the shared vehicle 102, such as a dash or windshield. Alternatively, in one embodiment, the housing is adapted for retrofitting into a particular make and model of the shared vehicle 102, such as in place of an eye-glass holder. In some embodiments, an in-vehicle sensing system 104 further includes additional external sensors 120 arranged on or throughout the shared vehicle 102, which are operably connected to the in-vehicle sensing module 112 via one or more communication buses 124. In some embodiments, the sensors 116, 120 used by the in-vehicle sensing module 112 may be specific to particular make and model of the shared vehicle 102.

In addition to the in-vehicle sensing system 104, the shared vehicle 102 includes a vehicle electronic control unit ("ECU") 128, a drive system 132, and a vehicle battery 136. In one embodiment, the vehicle ECU 128 is configured to operate the drive system 132, as well as various electronics of the vehicle, such as lights, locks, speakers, displays, etc. The vehicle ECU 128 may communicate with these various electronics and the drive system 132, as well with as the in-vehicle sensing module 112, via the one or more communication buses 124. In one embodiment, the vehicle ECU 128 communicates certain telemetric data to the in-vehicle sensing module 112, such as vehicle speed or travel direction and, thus, the vehicle ECU 128 may be considered one of the external sensors 120. The drive system 132 of the shared vehicle 102 includes a drive motor, for example an internal combustion engine and/or one or more electric motors, that drives the wheels of the shared vehicle 102, and the steering and braking components that enable the shared vehicle 102 to be moved in a controlled manner. The vehicle battery 136 is configured to provide operating power via a power line 140 (e.g., a 12V power line, such as the always-on power line or the switched/accessory power line of the shared vehicle 102) to the in-vehicle sensing module 112, the external sensors 120, the vehicle ECU 128, and/or any other vehicle electronics of the shared vehicle 102.

The in-vehicle sensing module 112 is configured to monitor a status of at least the cabin 108 of the vehicle. Particularly, the in-vehicle sensing module 112 is configured to process sensor data received from the sensors 116, 120 to infer one or more conditions, qualities, or statuses of the shared vehicle 102. For example, the in-vehicle sensing module 112 may detect whether the shared vehicle 102 is clean/dirty, that the shared vehicle 102 has been damaged or involved in a collision, whether the shared vehicle 102 has been subjected to cigarette smoke or other unpleasant smells, and/or whether an object has been left behind in the shared vehicle 102. The in-vehicle sensing module 112 utilizes appropriate algorithms, models (e.g., artificial neural networks), or thresholds to interpret the sensor data and enrich the data with metadata and event detection. It will be appreciated by those of ordinary skill in the art that the term "metadata" refers to any data that describes or gives information about other data (e.g., the sensor data).

To this end, depending on the particular conditions, qualities, or statuses of the shared vehicle 102 to be monitored, the sensors 116, 120 may comprise a wide variety of sensors including cameras, microphones, gyroscopes, accelerometers, smoke detectors, gas sensors, or other air-quality/particle sensors, temperature sensors, and/or humidity sensors. In one embodiment, the external sensors 120 include a vehicle camera arranged within the cabin 108 to capture images of the cabin 108, such as one native to the shared vehicle or one installed after-market. In one embodiment, the external sensors 120 includes a gyroscope/accelerometer module may include, for example, a microphone, a gyroscope, and an accelerometer integrated in a single housing that is affixed to the chassis of the shared vehicle 102.

The in-vehicle sensing module 112 is configured to upload, by a cellular Internet connection, relevant sensor data, event data, or other metadata to a cloud storage backend 150 for storage thereat. The data uploaded to the cloud storage backend 150 is accessible by a third-party cloud backend 160. The third-party backend 160 is, for example, associated with the shared vehicle service discussed above, such as a car rental service, an autonomous taxi service, or a ride sharing service. In this way, an operator of the shared vehicle service can monitor the condition of the shared vehicle 102, enforce rules and policies, and provide additional benefits to the customer with minimal human intervention.

In-Vehicle Sensing Module

Figure 2:
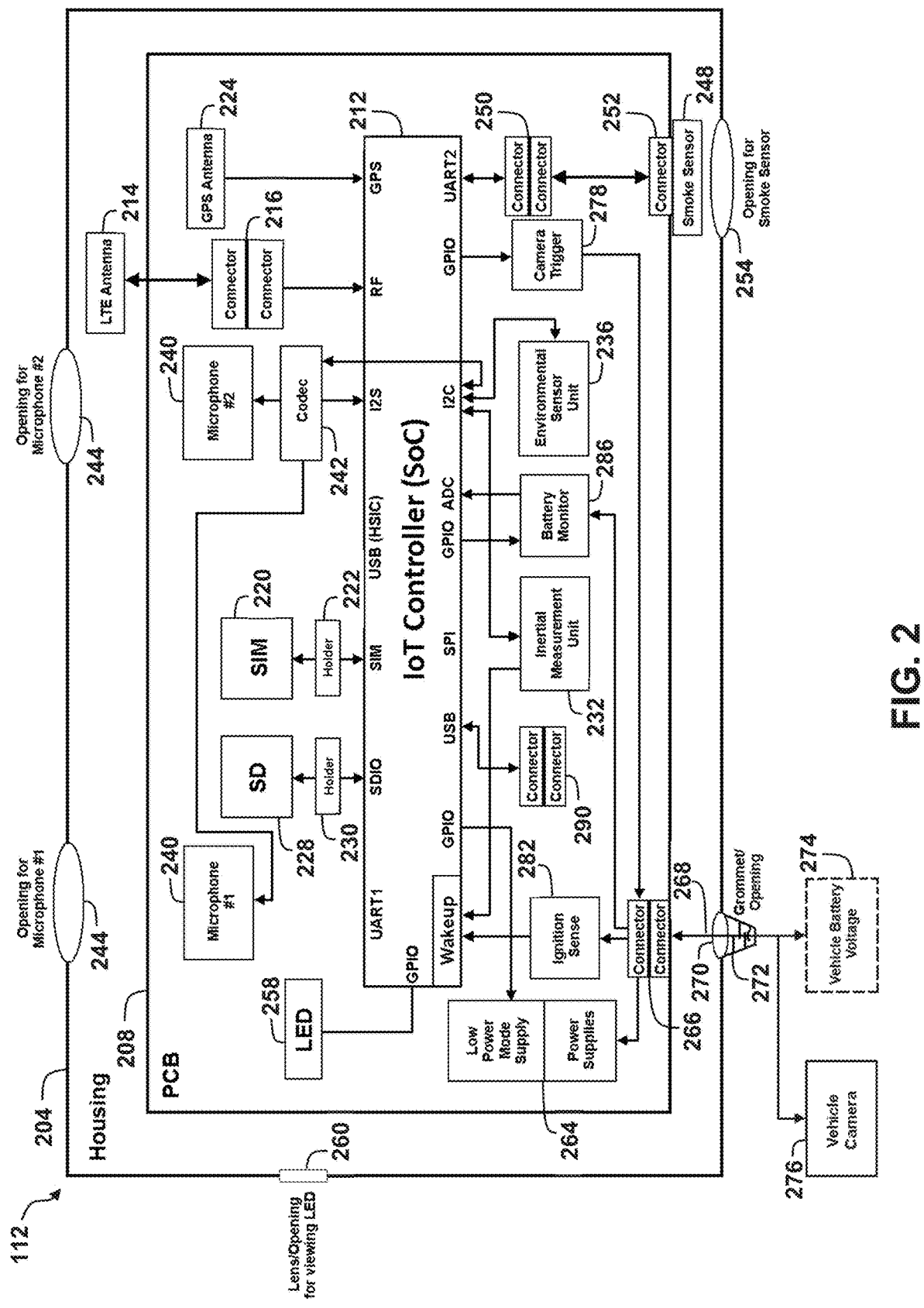
FIG. 2 shows exemplary electronic components of the in-vehicle sensing module of FIG. 1.

With reference to FIG. 2, exemplary components of one embodiment of the in-vehicle sensing module 112 are described. The in-vehicle sensing module 112 comprises a housing 204, within which at least one printed circuit board (PCB) 208 is contained and mounted. The PCB 208 supports and electrically interconnects a plurality of electrical components, at least including a controller 212 configured to operate the in-vehicle sensing module 112.

The controller 212 at least includes a processor and associated memory. It will be recognized by those of ordinary skill in the art that a "processor" includes any hardware system, hardware mechanism or hardware component that processes data, signals or other information. Accordingly, the processor may include a system with a central processing unit, graphics processing units, multiple processing units, dedicated circuitry for achieving functionality, programmable logic, or other processing systems. The memory may be any type of device capable of storing information accessible by the processor, such as a flash memory card, ROM, RAM, hard drives, discs, or any of various other computer-readable media serving as volatile or non-volatile data storage devices, as will be recognized by those of ordinary skill in the art. The memory is configured to store program instructions that, when executed by the processor, enable the in-vehicle sensing module 112 to perform various operations, including monitoring the cabin 108 of the shared vehicle 102, as described below.

In the illustrated embodiment, the controller 212 takes the form of an Internet of Things (IoT) controller 212, which has integrated features and functionalities beyond that of a generic multi-purpose controller. To this end, in the illustrated embodiment, the IoT controller 212 is configured as a system on a chip (SoC), which is arranged on the PCB 208. Alternatively, the IoT controller 212 may be equivalently configured as a system on a module (SoM) in which the sub-components thereof are arranged on at least one discreet PCB, which is connected to the PCB 208 by a cable and/or a module connector. In either case, the IoT controller 212 includes integrated features and functionalities beyond the processor and memory.

In some embodiments, the IoT controller 212 advantageously provides integrated cellular telephony functionality. To this end, the IoT controller 212 comprises a cellular telephony modem and/or transceiver as well as any other processors, memories, oscillators, or other hardware conventionally included in a cellular telephony module. The cellular telephony modem is configured to communicate with the Internet via wireless telephony networks, such as Global System for Mobiles (GSM), Code Division Multiple Access (CDMA), and/or Long-Term Evolution (LTE) networks. It should be appreciated that in alternative embodiments, a discreet cellular telephony module can be provided on the PCB 208 that is separate from the controller 212.

The cellular telephony modem of the IoT controller 212 is connected to a cellular antenna 214 via an antenna connector 216 that is arranged on the PCB 208. In at least one embodiment, the cellular antenna 214 is arranged within the housing 204, but separate from the PCB 208 and may, for example, comprise a flexible antenna that is mounted along interior side walls of the housing 204 or in some other manner designed to improve cellular reception of the in-vehicle sensing module 112. The cellular telephony modem further connects with a subscriber identity module ("SIM") card 220 that is inserted into a SIM card holder 222 that is arranged on the PCB 208 and configured to connect the SIM card 220 to the IoT controller 212. The SIM card 220 provides identifying information to enable the cellular telephony modem to access the wireless telephony network, as is generally known in the art.

In some embodiments, the IoT controller 212 advantageously provides integrated Global Navigation Satellite System (GNSS) functionality. To this end, the IoT controller 212 comprises a GNSS receiver as well as any other processors, memories, oscillators, or other hardware conventionally included in a GNSS module. The GNSS receiver is configured to receive signals from GNSS satellites from which location data can be determined. The GNSS receiver is configured to support one or more of, for example, GPS, GLONASS, BeiDou, and Galileo, or any other GNSS. The GNSS receiver is connected to a GNSS antenna 224 to enable reception of the GNSS signals. In the illustrated embodiment, the GNSS antenna 224 is arranged in or on the PCB 208, but can alternatively be arranged separately inside or outside the housing 204. It should be appreciated that in alternative embodiments, a discreet GNSS module can be provided on the PCB 208 that is separate from the controller 212.

In some embodiments (not shown), the IoT controller 212 may further include integrated Bluetooth® and/or Wi-Fi® transceivers configured to communicate locally with a smartphone or other smart device in the possession of the passenger or driver using the shared vehicle 102. Likewise, in some embodiments, discreet Bluetooth® and/or Wi-Fi® transceivers can be provided on the PCB 208 that are separate from the controller 212.

Finally, in some embodiments, the IoT controller 212 advantageously comprises a variety of integrated data/peripheral interfaces for operably connecting with a variety of additionally components of the in-vehicle sensing system 104, including general-purpose input/output (GPIO), Serial Peripheral Interface (SPI), Inter-Integrated Circuit (I²C or I2C), Inter-IC Sound (I²S or I2S), Secure Digital Input Output (SDIO), Universal Serial Bus (USB), USB High Speed Inter-Chip (HSIC), and universal asynchronous receiver-transmitter (UART). In this way, the IoT controller 212 provides easy compatibility with a variety of external sensors 120 that might be available within the shared vehicle 102, as well as providing compatibility with a variety of configurations of integrated sensors 116.

As noted above, the in-vehicle sensing module 112 includes one or more integrated sensors 116 configured to monitor a status of the shared vehicle 102 or at least the cabin 108 thereof. These integrated sensors 116 can be integrated directly with the IoT controller 212, arranged on the PCB 208, or otherwise arranged within the housing 204 separate from the PCB 208. The IoT controller 212 is configured to receive sensor data from the integrated sensors 116, as well as any external sensor 120, and write the sensor data to a non-volatile memory. Moreover, the IoT controller 212 is configured to process the sensor data to determine a variety of metadata, which is also written to the non-volatile memory. To this end, in the illustrated embodiment, the IoT controller 212 is connected to a removable memory storage device 228 that is inserted into a removable storage medium holder 230 that is arranged on the PCB 208 and configured to connect the removable memory storage device 228 to the IoT controller 212 (e.g., via SDIO). The removable memory storage device 228 may, for example, comprise a secure digital (SD), SD High Capacity (SDHC), or SD Extended Capacity (SDXC) memory card, as well as any equivalent type of removable memory card or other non-volatile memory technology.

In the illustrated embodiment, the integrated sensors 116 include an inertial measurement unit (IMU) 232 that is arranged on the PCB 208 and connected with the IoT controller 212 (e.g., via I²C). The IMU 232 includes one or more gyroscope sensors and one or more accelerometers. In one embodiment, the IMU 232 comprises an integrated 6-axis inertial sensor that provides both triaxial acceleration measurements and triaxial gyroscopic measurements. As will be discussed further below, in at least some embodiments, the in-vehicle sensing module 112 switches from a low power mode to an active state in response to measurements from the IMU 232. In other words, the IMU 232 may provide a wakeup signal for the IoT controller 212.

In the illustrated embodiment, the integrated sensors 116 include an environmental sensor 236 that is arranged on the PCB 208 and connected with the IoT controller 212 (e.g., via I²C). The environmental sensor 236 is configured to detect properties indicative of the air quality in the cabin such as relative humidity, barometric pressure, temperature, and presence of organic compounds, more particularly volatile organic compounds ("VOCs"). Accordingly, the environmental sensor 236 includes a variety of individual sensors integrated into a single package. However, it should be appreciated that individual discreet sensors may alternatively be provided, including a VOC sensor, a humidity sensor, a barometric pressure sensor, and a temperature sensor.

In the illustrated embodiment, the integrated sensors 116 include at least one microphone 240 that is arranged on the PCB 208 and connected with the IoT controller 212 (e.g., via I²S and/or I²C). The microphone 240 comprises any type of acoustic sensor configured to record sounds within the cabin 108. In at least one embodiment, the integrated sensors 116 include at least two microphones 240 spaced apart from one another on the PCB 208 so as to record stereo audio of the cabin 108. In one embodiment, the microphone(s) 240 take the form of Micro-Electro-Mechanical Systems (MEMS) microphones mounted directly on the PCB 208. In at least one embodiment, the microphone(s) 240 are connected to the IoT controller 212 via a hardware audio codec 242 configured to, for example, perform analogue-to-digital conversion of audio from the microphone(s) 240, amplify the audio from the microphone(s) 240, filter the audio from the microphone(s) 240, or otherwise encode or process the audio from the microphone(s) 240 for suitable usage by the IoT controller 212. In one embodiment, the housing 204 defines openings or groups of openings 244, which are situated near the microphone(s) 240 on the PCB 208 and which allow for exchange of air between the exterior of the housing 204 and the interior space of the housing 204 near the microphone(s) 240. In one embodiment, each of the microphone(s) 240 is surrounded by an acoustic seal gasket (not shown), one end of which seals against the PCB 208. The acoustic seal gaskets acoustically isolate the microphone(s) 240 so as to reduce interference in the sound transmitted through the openings 244 and detected by the microphone(s) 240.

In the illustrated embodiment, the integrated sensors 116 include a particle sensor 248 that is connected with the IoT controller 212 (e.g., via UART). The particle sensor 216 is configured to sense particulate matter concentrations in the ambient air of the cabin 108. The particle sensor 248 is at least configured to detect particulate matter having sizes or masses associated with smoke and, in particular, with tobacco smoke and/or marijuana smoke, but may also detect particulate matter associated with other airborne particles or water vapor. In at least one embodiment, the particle sensor 248 is arranged within the housing 204 separate from the PCB 208 and is connected with the IoT controller 212 by way of a cable that connects a connector 250 arranged on the PCB 208 with a connector 252 of the particle sensor 248. In one embodiment, the housing 204 defines an opening or group of openings 254, which is situated near the particle sensor 248 and which allows for exchange of air between the exterior of the housing 204 and the interior space of the housing 204 near the particle sensor 248.

In the illustrated embodiment, the in-vehicle sensing module 112 includes an indicator light (e.g. an LED) 258 mounted on the PCB 208 or the housing 204. The indicator light 258 is arranged so as to be visible through a transparent lens or opening 260 of the housing 204. The IoT controller 212 is configured to operate the indicator light 258 to emit light that indicates an operating status of the in-vehicle sensing module 112.

In the illustrated embodiment, the in-vehicle sensing module 112 further includes power supplies 264 configured to convert power from the vehicle battery 136 to suitable voltages for providing power to the IoT controller 212 and other components of the in-vehicle sensing module 112. In at least one embodiment, the power supplies 264 include a low power supply configured to provide power only to a select subset of components of the in-vehicle sensing module 112 in a low power mode of the in-vehicle sensing module 112. The power supplies 264 are connected to an external I/O connector 266, via which the power supplies 264 receive input power from the from the vehicle battery 136. It should be appreciated that, in some embodiments, the PCB 208 includes or is operably connected to a battery (not shown) as a secondary power source if the power from the vehicle battery 136 is interrupted.

In the illustrated embodiment, the in-vehicle sensing module 112 further includes an external cable 268 that connects to the external I/O connector 266 and exits the housing 204 via an opening 270 defined therein. In one embodiment, the external cable 268 includes a grommet 272 arranged at the opening 270, which is configured to attach the external cable 268 to the housing 204 at the opening 270 to provide strain relief. The external cable 268 is configured to connect with one or more vehicle interfaces, busses, or systems of the shared vehicle 102, at least including the power line 140, via one or more wire harnesses, or equivalent, so as to receive a vehicle battery voltage 274 (e.g. 12V) from the vehicle battery 136. Additionally, in at least some embodiments, the external cable 268 is configured to connect with the one or more communication buses 124 so as to receive data from external sensors 120 and/or from the vehicle ECU 128.

In the illustrated embodiment, the one or more external sensors 120 includes a vehicle camera 276 that is arranged within the shared vehicle 102 and configured to capture images of the cabin 108. The vehicle camera 276 may be a pre-existing camera that is native the make and model of the shared vehicle 102, or may be a camera that has been installed in the shared vehicle 102 after-market. The in-vehicle sensing module 112 includes camera trigger circuitry 278 arranged on the PCB 208 that connects to the external I/O connector 266 and to the IoT controller 212 (e.g., via GPIO). The IoT controller 212 is configured to operate the camera trigger circuitry 278 to activate the vehicle camera 276 to capture one or more images or video inside the cabin 108. The IoT controller 212 is configured to receive the captured images from the vehicle camera 276 via camera trigger circuitry 278 or via another data connection.

In the illustrated embodiment, the in-vehicle sensing module 112 further includes ignition sensing circuitry 282 arranged on the PCB 208 and connected to the external I/O connector 266 and to the IoT controller 212. The ignition sensing circuitry 282 is configured to monitor the voltage of the power line 140 provided via the external I/O connector 266 and determine when an ignition of the shared vehicle 102 has been activated. The ignition sensing circuitry 282 then transmits an ignition signal to the IoT controller 212 indicating that the shared vehicle 102 has been started. As will be discussed further below, in at least some embodiments, the in-vehicle sensing module 112 switches from a low power mode to an active state in response to the ignition signal. In other words, the ignition signal may act as a wakeup signal for the IoT controller 212.

In the illustrated embodiment, the in-vehicle sensing module 112 further includes battery monitoring circuitry 286 arranged on the PCB 208 and connected to the external I/O connector 266 and to the IoT controller 212 (e.g., via GPIO and/or an ADC input). The battery monitoring circuitry 286 and/or the IoT controller 212 are configured to monitor a voltage and current of the power line 140 provided via the external I/O connector 266. In some embodiments, a power state of the in-vehicle sensing module 112 (e.g., off, on, low power mode, active mode) is controlled or changed depending on the voltage and current of the power line 140.

Finally, in the illustrated embodiment, the in-vehicle sensing module 112 further includes an external device connector 290 arranged on the PCB 208 and connected to the external I/O connector 266 and to the IoT controller 212 (e.g., via USB). The external device connector 290 enables an external computing device, such as a diagnostic tool or the like, to be temporarily connected to the in-vehicle sensing module 112 to read or receive data from the in-vehicle sensing module 112. The external device connector 290 may, for example, take the form of a USB connector (e.g. USB-A, USB-C, micro-USB, etc.) or the like, configured to enable wired communication between the IoT controller 212 and the external computing device.

Operation of the In-Vehicle Sensing Module

A variety of methods and processes are described below for operating the in-vehicle sensing module 112. In these descriptions, statements that a method, processor, and/or system is performing some task or function refers to a controller or processor (e.g., the IoT controller 212 of the in-vehicle sensing module 112) executing programmed instructions stored in non-transitory computer readable storage media (e.g., the memory of the IoT controller 212 of the in-vehicle sensing module 112 or the removable memory storage device 228) operatively connected to the controller or processor to manipulate data or to operate one or more components in the vehicle monitoring system 100 to perform the task or function. Additionally, the steps of the methods may be performed in any feasible chronological order, regardless of the order shown in the figures or the order in which the steps are described.

Figure 3:
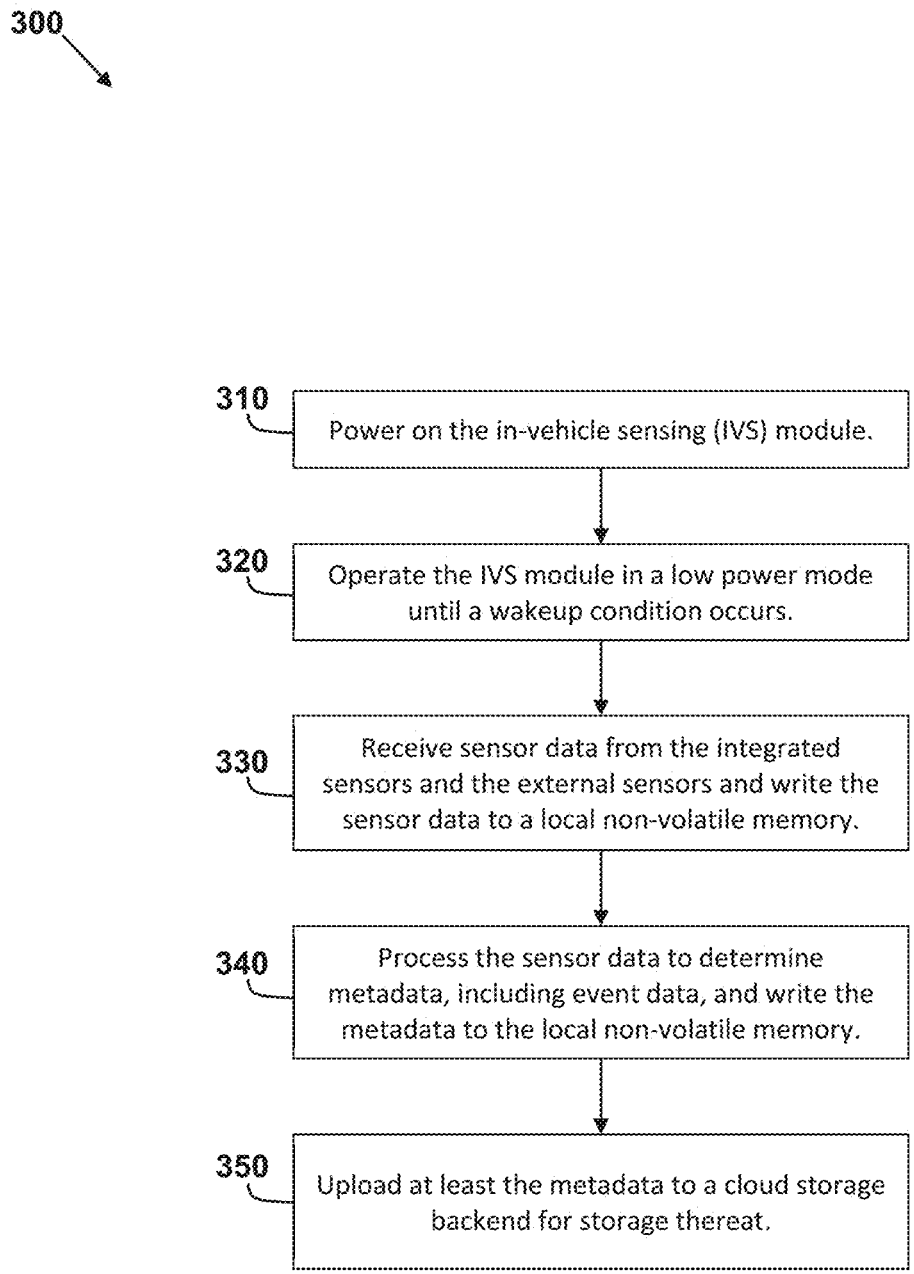
FIG. 3 shows a method for operating the in-vehicle sensing module of FIG. 1 to monitor at least a cabin of a shared vehicle.

FIG. 3 shows a method 300 for operating the in-vehicle sensing module 112 to monitor at least the cabin 108 of a shared vehicle 102. The method 300 advantageously captures, and stores in a non-volatile memory, sensor data during operation of the shared vehicle 102, for example in the context of a shared vehicle service, such as car rental service, an autonomous taxi service, a ride sharing service, or the like. Moreover, the method 300 advantageously processes the sensor data to provide metadata, which is also stored in the non-volatile memory. The method 300 advantageously enables operators of such shared vehicle services to monitor the condition of the shared vehicle 102, enforce rules and policies, and provide additional benefits to the customer with minimal human intervention.

The method 300 begins with powering on the in-vehicle sensing module (block 310). Particularly, as noted above, the battery monitoring circuitry 286 is configured to monitor a voltage and current of the power line 140 provided via the external I/O connector 266. In some embodiments, the power line 140 connected to via the external I/O connector 266 is an always-on power line of the shared vehicle 102, which directly provides the battery voltage of the vehicle battery 136. It will be appreciated that, if precisely measured, the battery voltage of the vehicle battery 136 can be used to estimate a state of charge of the vehicle battery 136. In one embodiment, the battery monitoring circuitry 286 measures the battery voltage provided via the power line 140 and, in response to the battery voltage exceeding a predetermined threshold voltage, provides a turn-on signal to the IoT controller 212 to at least partially turn on the in-vehicle sensing module 112. The predetermined threshold voltage is a battery voltage corresponding to a predetermined state of charge of the vehicle battery. In one embodiment, the predetermined state of charge is one at which the vehicle battery 136 can still provide sufficient amperage to start the vehicle. In this way, the in-vehicle sensing module 112 will only operate with battery power if the vehicle battery 136 is sufficiently charged and will not cause the vehicle battery to unnecessarily drain if the shared vehicle 102 is not started for an extended period of time.

In alternative embodiments, the power line 140 connected to via the external I/O connector 266 is a switched/accessory power line of the shared vehicle 102, which only provides the battery voltage of the vehicle battery 136 if the ignition has been activated to start the shared vehicle 102 (generally by toggling an operating element of the ignition while pressing the brakes) or if accessory power of the shared vehicle 102 has been activated (generally by toggling an operating element of the ignition without pressing the brakes). Thus, in response to detecting the battery voltage from the vehicle battery 136, the battery monitoring circuitry 286 provides a turn-on signal to the IoT controller 212 to at least partially turn on.

The method 300 continues with operating the in-vehicle sensing module in a low power mode until a wakeup condition occurs (block 320). Particularly, in response to the turn-on signal, the in-vehicle sensing module 112 begins operation in a low power mode in which the IoT controller 212 activates a subset of components of the in-vehicle sensing module 112 to turn on. Particularly, in one exemplary embodiment, in the low-power mode, only the IMU 232, the environmental sensor 236, the ignition sensing circuitry 282, and the low power supply of the power supplies 264 are activated. Additionally, the IoT controller 212 itself may operate in a low power state in which certain functionalities or sub-components, such as those related to cellular telephony and GNSS, are disabled.

The in-vehicle sensing module 112 operates in the low power mode until a wakeup condition is satisfied or, more particularly, until the IoT controller 212 receives a wakeup signal. In response to receiving the wakeup signal, the in-vehicle sensing module 112 begins operation in an active mode in which the IoT controller 212 activates all of the components of the in-vehicle sensing module 112 to turn on. In one embodiment, the ignition sensing circuitry 282 sends a wakeup signal to the IoT controller 212 in response to detecting that the ignition of the shared vehicle 102 has been activated. In one embodiment, the IMU 233 sends a wakeup signal to the IoT controller 212 in response to detecting a disturbance of the shared vehicle 102 (e.g., acceleration or gyroscopic measurements exceeding a threshold or matching a predetermined profile) indicating, for example, that a driver has unlocked the shared vehicle 102 and entered the cabin 108. In one embodiment, if the cellular telephony functionality of the IoT controller 212 is operational during low-power mode, the wakeup signal can be received from the cloud storage backend 150.

The method 300 continues with receiving sensor data from the integrated sensors and the external sensors and writing the sensor data to a local non-volatile memory (block 330). Particularly, in the active mode, after receiving the wakeup signal, the IoT controller 212 begins recording/writing sensor data from the integrated sensors 116 and from the external sensors 120 to the removable memory storage device 228 or to some other non-volatile memory. In one embodiment, the IoT controller 212 implements one or more ring buffers (which may also be referred to as circular buffers, circular queues, or a cyclic buffers) on the removable memory storage device 228 to manage storage of newly measured sensor data and the deletion of old sensor data.

The method 300 continues with processing the sensor data to determine metadata, including event data, and writing the metadata to the local non-volatile memory (block 340). Particularly, the IoT controller 212 is configured to process the sensor data received from the integrated sensors 116 or from the external sensors 120 to enrich the data with metadata and, in particular, event detection. As discussed above, the sensors 116, 120 may comprise a wide variety of sensors including cameras, microphones, gyroscopes, accelerometers, smoke detectors or other air-quality/particle sensors, temperature sensors, and/or humidity sensors. The IoT controller 212 processes the sensor data to determine one or more conditions, qualities, or statuses of the shared vehicle 102 and/or detect the occurrence of one or more events related to the one or more conditions, qualities, or statuses of the shared vehicle 102. The IoT controller 212 stores the determined conditions, qualities, or statuses and the detected events related thereto on the removable memory storage device 228 as metadata of the stored sensor data.

In at least some embodiments, the IoT controller 212 is configured to determine one or more conditions, qualities, or statuses of the shared vehicle 102 and/or detect the occurrence of one or more events related to the one or more conditions, qualities, or statuses of the shared vehicle 102, using an algorithm or model, such as a machine learning model (e.g., an artificial neural network). In one embodiment, the IoT controller 212 is configured to receive updates for the algorithm or model from the cloud storage backend 150, via the cellular telephony modem thereof.

In some embodiment, in response to detecting a particular quality, condition, status, or event, the IoT controller 212 operates the camera trigger circuitry 278 to cause the vehicle camera 276 to capture an image or video of the cabin 108. The IoT controller 212 stores the captured image on the removable memory storage device 228 as metadata of the sensor data from which the particular quality, condition, status, or event was detected.

In some embodiments, the IoT controller 212 is configured to determine whether the shared vehicle 102 has been involved in a collision or has been otherwise mechanically damaged based on the acceleration and gyroscopic measurements provided by the IMU 232 or by a similar external sensor 120. In one embodiment, the IoT controller 212 is configured to detect a collision or damage event in response to the acceleration and/or the gyroscopic measurements exceeding a predetermined threshold or matching with a predetermined acceleration profile. In one embodiment, the IoT controller 212 executes a machine learning model (e.g., an artificial neural network) to detect a collision or damage event based on the acceleration and/or the gyroscopic measurements. In one embodiment, the IoT controller 212 detects where the damage occurred (e.g., front left) and classifies a severity or grade of damage (e.g., hard), based on the acceleration and/or the gyroscopic measurements or other sensor data. In one embodiment, the IoT controller 212 executes a machine learning model (e.g., an artificial neural network) to classify the detected a collision or damage based on the acceleration and/or the gyroscopic measurements. In one embodiment, in response to a collision or damage event, the IoT controller 212 operates the camera trigger circuitry 278 to cause the vehicle camera 276 to capture an image or video of the cabin 108.

In some embodiments, the IoT controller 212 is configured to determine whether the cabin 108 of the shared vehicle 102 has an unpleasant or abnormal odor based on the VOC measurements provided by the environmental sensor 236. In one embodiment, the IoT controller 212 is configured to detect an unpleasant/abnormal odor event in response to the VOC measurements exceeding a predetermined threshold or matching with a predetermined profile. In one embodiment, the IoT controller 212 executes a machine learning model (e.g., an artificial neural network) to detect an unpleasant/abnormal odor event based on the VOC measurements. In one embodiment, in response to an unpleasant/abnormal odor event, the IoT controller 212 operates the camera trigger circuitry 278 to cause the vehicle camera 276 to capture an image or video of the cabin 108.

Additionally, the IoT controller 212 may be configured in some embodiments to identify and/or categorize the scents or smells present in the cabin 108 of the shared vehicle 102 based at least on the VOC measurements provided by the environmental sensor 236. For instance, based on the chemical profile of the VOCs sensed in the cabin 108, and, in some embodiments, in conjunction with the sensed temperature, humidity, barometric pressure, and particulate concentrations, the IoT controller 212 identifies the scent as corresponding to a particular category of odors. For example, in some embodiments, the IoT controller 212 is configured to identify and categorize odors corresponding to one or more of: marijuana, tobacco, perfume, food, beverages, alcohol, urine, vomit, feces, animal odors, mold, gasoline, and other odors that may be detectable to users of the vehicle 102. In one embodiment, the IoT controller 212 is configured to execute a machine learning model (e.g., an artificial neural network) to identify and categorize the odors in the vehicle cabin 108 based on the detected VOCs and, in some embodiments, further based on the temperature, humidity, pressure, and/or particle measurements. In some embodiments, in response to detection of certain categories of odors, the IoT controller 212 operates the camera trigger circuitry 278 to cause the vehicle camera 276 to capture an image or video of the cabin 108.

In some embodiments, the IoT controller 212 is configured to determine whether a driver or passenger is smoking within the cabin 108 of the shared vehicle 102 based on the particulate matter measurements provided by the particle sensor 248. In one embodiment, the IoT controller 212 is configured to monitor a curve of the particulate matter concentrations over time and detect a smoking event in response to the curve of particulate matter concentrations matching the reference profile/curve or exceeding the threshold concentration. In one embodiment, the IoT controller 212 executes a machine learning model (e.g., an artificial neural network) to detect a smoking event based on the particulate matter measurements. In one embodiment, in response to a smoking event, the IoT controller 212 operates the camera trigger circuitry 278 to cause the vehicle camera 276 to capture an image or video of the cabin 108.

Figure 4:
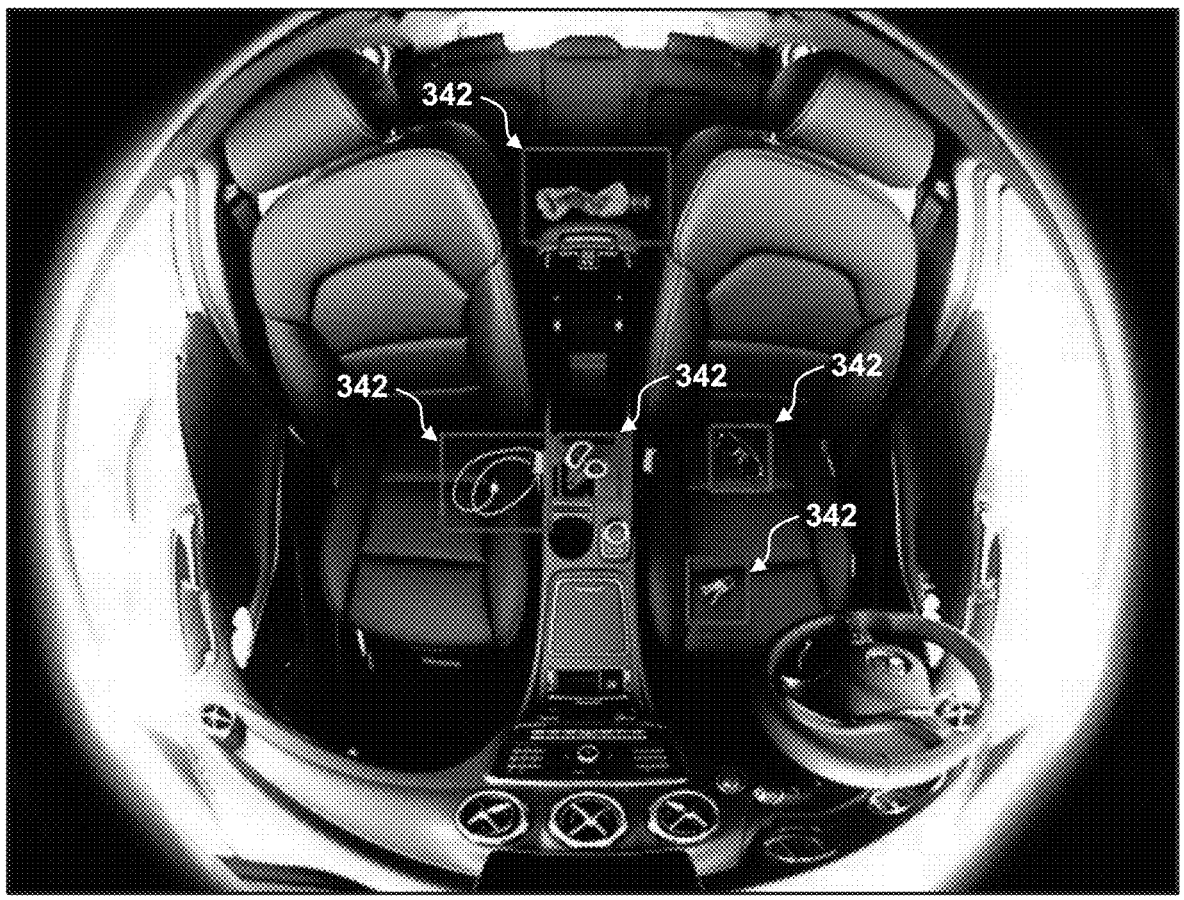
FIG. 4 shows a photo of the cabin of the shared vehicle in which left behind objects are marked with boxes.

In some embodiments, the IoT controller 212 is configured to detect whether objects have been left behind by passengers of the vehicle, such as phones, keys, or glasses, based on an image or video of the cabin 108. Particularly, the IoT controller 212 operates the camera trigger circuitry 278 to cause the vehicle camera 276 to capture an image or video of the cabin 108 after a driver or passenger leaves the shared vehicle 102. The IoT controller 212 executes an image analysis algorithm, such as a machine learning model (e.g., an artificial neural network), to analyze the captured image or video of the cabin 108 and detect lost or left behind objects in the shared vehicle 102. If a lost or left behind object is detected, then the IoT controller 212 stores a lost or left behind object event in the metadata. In one embodiment, the IoT controller 212 modifies the captured image or video to mark the lost or left behind objects in the captured image or video, such as with boxes 342 as shown in FIG. 4, and also lists the objects in metadata of the image or video. In one embodiment, the IoT controller 212 distinguishes and classifies the lost or left behind objects, for example using as a machine learning model (e.g., an artificial neural network), and includes these classifications in the metadata.

Figure 5:
FIG. 5 shows a photo of the cabin of the shared vehicle in which dirt on the floor of the vehicle is marked with boxes.
Figure 6:
FIG. 6 shows a photo of the cabin of the shared vehicle in which debris on the floor and seats of the vehicle is marked with boxes.

In some embodiments, the IoT controller 212 is configured to detect whether the cabin 108 of the vehicle is clean or dirty, based on an image or video of the cabin 108. Particularly, the IoT controller 212 operates the camera trigger circuitry 278 to cause the vehicle camera 276 to capture an image or video of the cabin 108 after a driver or passenger leaves the shared vehicle 102. The IoT controller 212 executes an image analysis algorithm, such as a machine learning model (e.g., an artificial neural network), to analyze the captured image or video to detect dirt or debris in the shared vehicle 102. Dirt can assume several forms including dust, different varieties of soil, debris, or scattered pieces of rubbish or remains. Common examples include sand or grass on the floor of the cabin 108, as shown in FIG. 5, and crumbs or other debris on the floor or seats of the cabin 108, as shown in FIG. 6. If dirt or debris is detected, then the IoT controller 212 stores a dirt or debris event in the metadata. The IoT controller 212 modifies the captured image or video to mark the dirt or debris in the image or video, such as with boxes 344, 346 as shown in FIG. 5 and FIG. 6, and also lists the dirt or debris in metadata of the image or video. In one embodiment, the IoT controller 212 classifies the detected dirt or debris (e.g., removable/not removable, trash, dangerous, liquid, etc.), for example using as a machine learning model (e.g., an artificial neural network), and includes these classifications in the metadata.

Returning to FIG. 3, the method 300 continues with uploading at least the metadata to a cloud storage backend for storage thereat (block 350). Particularly, the IoT controller 212 is configured to operate the cellular telephony modem thereof to upload at least the determined metadata to the cloud storage backend 150. The uploaded metadata at least includes the detected events and may include corresponding timestamps indicating the time at which each event occurred, as well as other contextual information regarding the detected events (e.g., an image captured in response to detecting an event). In some embodiments, the IoT controller 212 is configured to also upload the raw sensor data from which an event was detected, or intermediate data determined during the processing of the sensor data to detect an event. In some embodiments, the IoT controller 212 is configured to upload all of the raw sensor data, regardless of whether the sensor data correspond to any detected events. In one embodiment, the in-vehicle sensing module 112 utilizes a secured and encrypted (TLS V1.2 encryption) connection to the cloud storage backend 150 using a public key infrastructure (PKI), or equivalent. In one embodiment, authentication is ensured by usage of certificates, which are signed by appropriate certificate authorities.

Cloud Storage Backend

Figure 7:
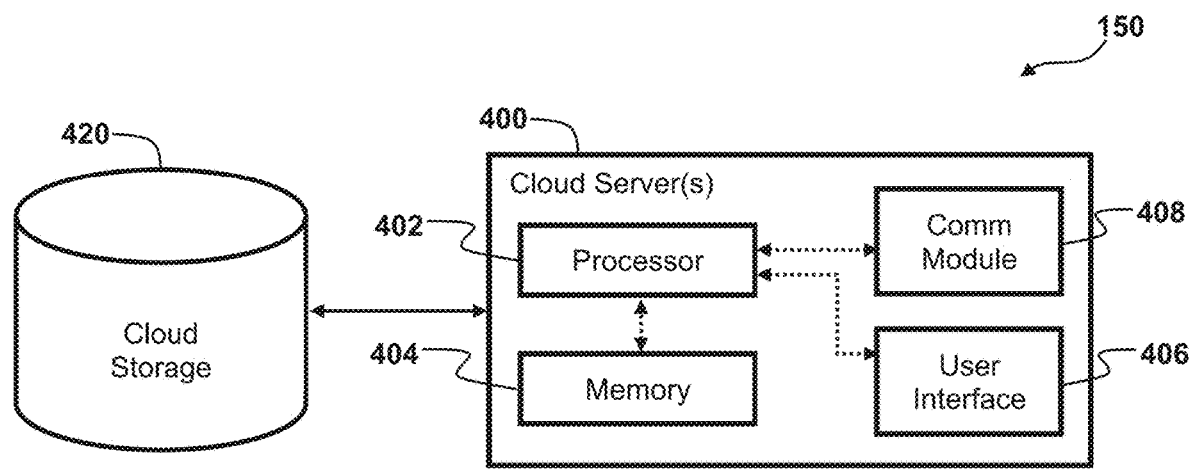
FIG. 7 shows exemplary components of the cloud storage backend of FIG. 1.

With reference now to FIG. 7, exemplary components of the cloud storage backend 150 are described. It will be appreciated that the components of the cloud storage backend 150 shown and described herein are merely exemplary and that the cloud storage backend 150 may comprise any alternative configuration.

As shown in FIG. 4, the exemplary embodiment of the cloud storage backend 150 comprises one or more cloud servers 400 and one or more cloud storage devices 420. The cloud servers 400 at least include one or more database servers configured to manage the sensor data, event data, and/or other metadata received from the in-vehicle sensing module 112 and stored in the cloud storage devices 420. Additionally, the cloud servers 400 may further include servers configured to serve a variety of other functions for the cloud storage backend, including web servers or application servers, depending on the features provided by cloud storage backend 150. Each of the cloud servers 400 includes, for example, a processor 402, a memory 404, a user interface 406, and a network communications module 408. It will be appreciated that the illustrated embodiment of the cloud servers 400 is only one exemplary embodiment of a cloud server 400 and is merely representative of any of various manners or configurations of a personal computer, server, or any other data processing system that is operative in the manner set forth herein.

The processor 402 is configured to execute instructions to operate the cloud servers 400 to enable the features, functionality, characteristics and/or the like as described herein. To this end, the processor 402 is operably connected to the memory 404, the user interface 406, and the network communications module 408. The processor 402 generally comprises one or more processors which may operate in parallel or otherwise in concert with one another. It will be recognized by those of ordinary skill in the art that a "processor" includes any hardware system, hardware mechanism or hardware component that processes data, signals or other information. Accordingly, the processor 402 may include a system with a central processing unit, graphics processing units, multiple processing units, dedicated circuitry for achieving functionality, programmable logic, or other processing systems.

The cloud storage devices 420 are configured to store sensor data, event data, and/or other metadata received from the in-vehicle sensing module 112. The cloud storage devices 420 may be of any type of long-term non-volatile storage device capable of storing information accessible by the processor 402, such as hard drives or any of various other computer-readable storage media recognized by those of ordinary skill in the art. Likewise, the memory 404 is configured to store program instructions that, when executed by the processor 402, enable the cloud servers 400 to perform various operations described herein, including managing the sensor data, event data, and/or other metadata stored in the cloud storage devices 420. The memory 404 may be of any type of device or combination of devices capable of storing information accessible by the processor 402, such as memory cards, ROM, RAM, hard drives, discs, flash memory, or any of various other computer-readable media recognized by those of ordinary skill in the art.

The network communications module 408 of the cloud servers 400 provides an interface that allows for communication with any of various devices, at least including the in-vehicle sensing module 112. In particular, the network communications module 408 may include a local area network port that allows for communication with any of various local computers housed in the same or nearby facility. Generally, the cloud servers 400 communicate with remote computers over the Internet via a separate modem and/or router of the local area network. Alternatively, the network communications module 408 may further include a wide area network port that allows for communications over the Internet. In one embodiment, the network communications module 408 is equipped with a Wi-Fi transceiver or other wireless communications device. Accordingly, it will be appreciated that communications with the cloud servers 400 may occur via wired communications or via the wireless communications. Communications may be accomplished using any of various known communications protocols.

The cloud servers 400 may be operated locally or remotely by an administrator. To facilitate local operation, the cloud servers 400 may include a user interface 406. In at least one embodiment, the user interface 406 may suitably include an LCD display screen or the like, a mouse or other pointing device, a keyboard or other keypad, speakers, and a microphone, as will be recognized by those of ordinary skill in the art. Alternatively, in some embodiments, an administrator may operate the cloud servers 400 remotely from another computing device which is in communication therewith via the network communications module 408 and has an analogous user interface.

The cloud storage backend 150 is configured to store and manage the sensor data, event data, and/or other metadata on the cloud storage devices 420 in a secure way and provide access to the sensor data, event data, and/or other metadata by operators of the shared vehicle service, as well as other authorized third parties, via the third-party backend 160 or via a web interface or API that includes controlled access and identity management. To this end, in at least some embodiments the cloud storage backend 150 is in bi-directional communication with the third-party backend 160 of the shared vehicle service provider.

Operation of the Cloud Storage Backend

A variety of methods and processes are described below for operating the cloud storage backend 150. In these descriptions, statements that a method, processor, and/or system is performing some task or function refers to a controller or processor (e.g., the processor 402 of the cloud storage backend 150) executing programmed instructions stored in non-transitory computer readable storage media (e.g., the memory of the processor 402 of the cloud storage backend 150) operatively connected to the controller or processor to manipulate data or to operate one or more components in the vehicle monitoring system 100 to perform the task or function. Additionally, the steps of the methods may be performed in any feasible chronological order, regardless of the order shown in the figures or the order in which the steps are described.

Figure 8:
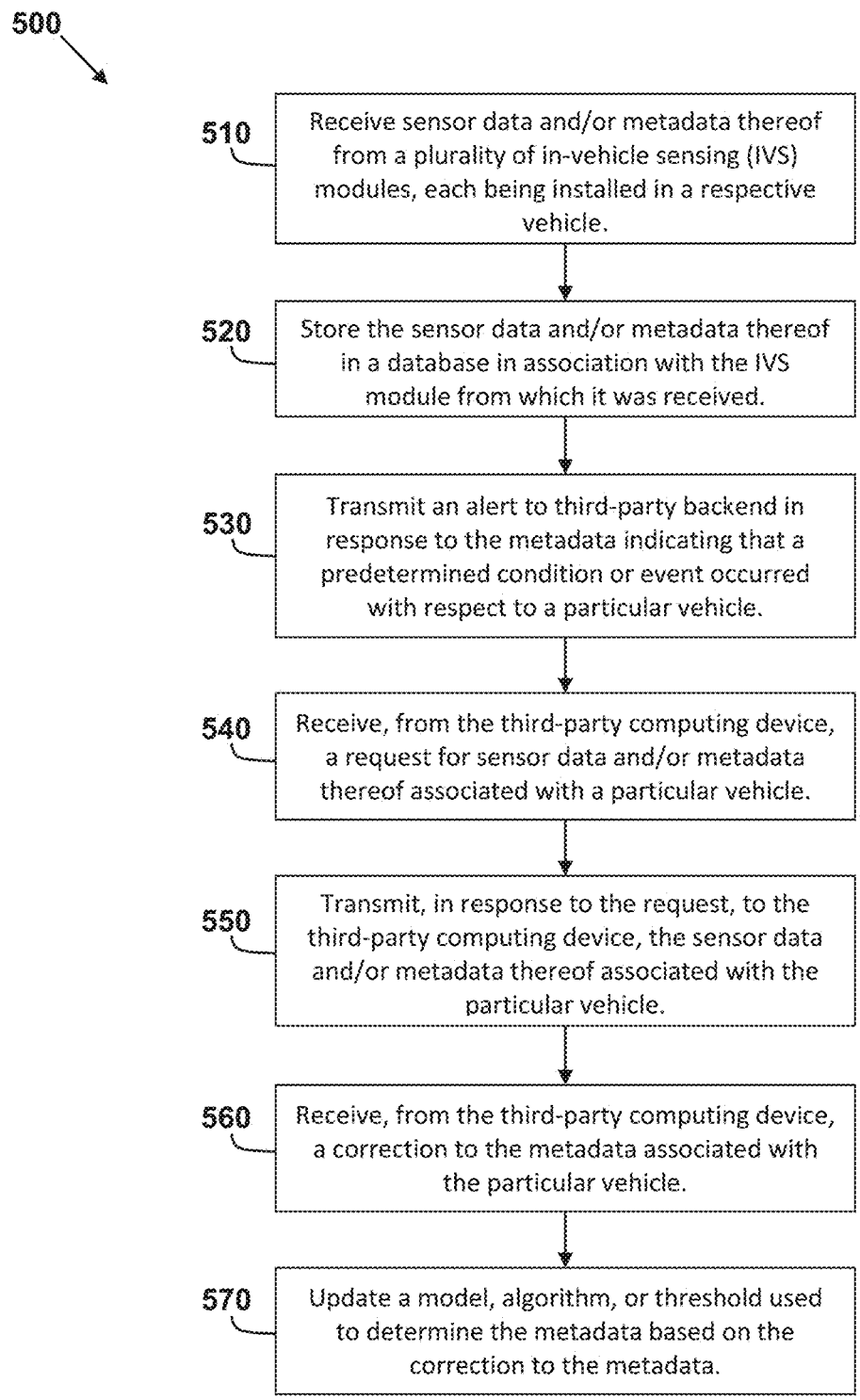
FIG. 8 shows a method for operating the cloud storage system of FIG. 1 to manage data uploaded from a plurality of in-vehicle sensing modules.

FIG. 8 shows a method 500 for operating the cloud storage system 150 to manage data uploaded from a plurality of in-vehicle sensing modules 112. The method 500 advantageously enables an operator of a shared vehicle service to access metadata regarding a monitoring of shared vehicles used by the shared vehicle service. In this way, the method 500 advantageously enables operators of such shared vehicle services to monitor the condition of the shared vehicles 102 in which the plurality of in-vehicle sensing modules 112 are installed, enforce rules and policies, and provide additional benefits to the customer with minimal human intervention.

The method 500 begins with receiving sensor data and/or metadata thereof from a plurality of in-vehicle sensing modules, each being installed in a respective vehicle (block 510). Particularly, the processor 402 of the cloud server(s) 400 of the cloud storage backend 150 operates the network communications module 408 to receive the sensor data and/or metadata uploaded by each of a plurality of in-vehicle sensing modules 112 installed in a plurality of shared vehicles 102, such as those of a vehicle fleet of a shared vehicle service. As noted above, the metadata indicates whether or not various conditions or events have occurred with respect to the shared vehicle 102 in which the in-vehicle sensing module 112 is installed. This metadata is determined by each in-vehicle sensing module 112 based on sensor data captured by the sensors of each in-vehicle sensing module 112.

The method 500 continues with storing the sensor data and/or metadata thereof in a database in association with the in-vehicle sensing module from which it was received (block 520). Particularly, the processor 402 stores the received sensor data and/or metadata in a database on the cloud storage devices 420 in association with the particular the in-vehicle sensing modules 112 from which the data was received. As used herein, to store data "in association" with some other data or concept means that a relationship or correlation is defined between the data and the other data or concept, such as with a tag, header, table, flag, index, data structure, or similar technique. For example, in one embodiment, the processor 402 tags or otherwise associates the sensor data and/or metadata in the database with a unique identifier of the particular in-vehicle sensing module 112 from which the sensor data and/or metadata was received or, equivalently, with a unique identifier of the shared vehicle 102 in which the respective in-vehicle sensing modules 112 is installed. In this way, the source for each set of sensor data and/or metadata is identifiable in the database.

The method 500 continues with transmitting an alert to third-party backend in response to the metadata indicating that a predetermined condition or event occurred with respect to a particular vehicle (block 530). Particularly, as noted above, the in-vehicle sensing modules 112 are configured to process sensor data to detect the occurrence of various predetermined conditions or events with respect to the corresponding shared vehicle 102. The metadata includes the result of this processing and may indicate, for example, whether the shared vehicle 102 has been involved in a collision or has been otherwise mechanically damaged, whether the cabin 108 of the shared vehicle 102 has an unpleasant or abnormal odor, whether a driver or passenger is smoking within the cabin 108 of the shared vehicle 102, whether objects have been left behind by passengers of the shared vehicle 102, and whether the cabin 108 of the shared vehicle 102 is clean or dirty.

If metadata indicates that a predetermined condition or event (such as one of those mention above) occurred with respect to the corresponding shared vehicle 102, the processor 402 is configured to operate the network communications module 408 to transmit an alert message to the third-party backend 160 or other remote third-party computing device (e.g., associated with an operator of the shared vehicle service) in response to receiving the metadata indicating that the predetermined condition or event occurred. In at least one embodiment, the alert message includes (1) an indication of what predetermined condition or event occurred, (2) a timestamp indicating when the predetermined condition or event occurred or was detected, and (3) a unique identifier of the in-vehicle sensing modules 112 by which the predetermined condition or event was detected or a unique identifier of the shared vehicle 102 in which the predetermined condition or event occurred. In one embodiment, the alert message is an email.

In this way, in the event of a rule or policy violation by a customer (e.g., a rule against smoking in the shared vehicle 102), the operator of the shared vehicle service is immediately notified and can take action against the customer, such as by fining or banning the customer. Similarly, the operator of the shared vehicle service can take actions to remedy the condition of the shared vehicle 102 (e.g., bring the shared vehicle 102 in for servicing, repair, or cleaning). Finally, a customer can be informed immediately in case of detecting a lost or left behind object.

The method 500 continues with receiving, from the third-party computing device, a request for sensor data and/or metadata thereof associated with a particular vehicle (block 540). Particularly, as mentioned above, the cloud storage backend 150 is configured to provide access to the sensor data and/or metadata by operators of the shared vehicle service, as well as other authorized third parties, via the third-party backend 160 or via a web interface or an application programming interface (API) that includes controlled access and identity management. To this end, the processor 402 operates the network communications module 408 to receive a request message that requests sensor data and/or metadata uploaded by a particular in-vehicle sensing module 112 or associated with a particular shared vehicle 102. The request message may be received from the third-party backend 160 or from some other authorized third-party computing device. The request message identifies the unique identifier of a particular in-vehicle sensing modules 112 or the unique identifier of a particular shared vehicle 102.

The method 500 continues with transmitting, in response to the request, to the third-party computing device, the sensor data and/or metadata thereof associated with the particular vehicle (block 550). Particularly, the processor 402 identifies the sensor data and/or metadata stored in the database of the cloud storage devices 420 that is associated with the unique identifier of a particular in-vehicle sensing modules 112 or the unique identifier of a particular shared vehicle 102, which was indicated in the request. The processor 402 of the cloud server(s) 400 of the cloud storage backend 150 then operates the network communications module 408 to transmit the identified the sensor data and/or metadata to the third-party backend 160 or other authorized third-party device, or otherwise make the identified the sensor data and/or metadata available thereto.

The method 500 continues with receiving, from the third-party computing device, a correction to the metadata associated with the particular vehicle (block 560). Particularly, the processor 402 of the cloud server(s) 400 of the cloud storage backend 150 operates the network communications module 408 to receive a correction message including correction of the metadata uploaded by a particular in-vehicle sensing module 112 or associated with a particular shared vehicle 102. The correction message may be received from the third-party backend 160 or from some other authorized third-party computing device. The correction message identifies a modification or alteration to the metadata uploaded by a particular in-vehicle sensing module 112 or associated with a particular shared vehicle 102. For example, the metadata may indicate that a particular event occurred, but upon further review by the shared vehicle service provider, it might be determined that the event did not occur. The correction may include a corrected value for some part of the metadata. Alternatively, the correction may simply identify that some part of the metadata that was incorrectly determined or that is otherwise erroneous, without providing a corrected or true value. The operator of the shared vehicle service can provide feedback by providing a correction of the metadata to the cloud storage backend 150.

The method 500 continues with updating a model, algorithm, or threshold used to determine the metadata based on the correction to the metadata (block 570). Particularly, as mentioned above, the IoT controller 212 of the in-vehicle sensing modules 112 utilize a variety of models, algorithms, or thresholds to process the sensor data and determine the metadata. In response to receiving a correction to the metadata, the processor 402 of the cloud server(s) 400 of the cloud storage backend 150 determine an update or refinement to one or more of these models, algorithms, or thresholds. Next, the processor 402 operates the network communications module 408 to transmit the update or refinement to the one or more of these algorithms, models, or thresholds to each of the in-vehicle sensing modules 112 for usage thereat, as applicable.

Embodiments within the scope of the disclosure may also include non-transitory computer-readable storage media or machine-readable medium for carrying or having computer-executable instructions (also referred to as program instructions) or data structures stored thereon. Such non-transitory computer-readable storage media or machine-readable medium may be any available media that can be accessed by a general purpose or special purpose computer. By way of example, and not limitation, such non-transitory computer-readable storage media or machine-readable medium can comprise RAM, ROM, EEPROM, CD-ROM or other optical disk storage, magnetic disk storage or other magnetic storage devices, or any other medium which can be used to carry or store desired program code means in the form of computer-executable instructions or data structures. Combinations of the above should also be included within the scope of the non-transitory computer-readable storage media or machine-readable medium.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method for managing data of a vehicle monitoring system, the vehicle monitoring system having a plurality of monitoring devices, each monitoring device of the plurality of monitoring devices being installed in a respective vehicle and having at least one sensor configured to capture respective sensor data, the method comprising:
receiving, at a server, from each respective monitoring device of the plurality of monitoring devices, respective metadata indicating whether at least one predetermined condition of the respective vehicle has occurred, the respective metadata being determined by the respective monitoring device based on the respective sensor data;
storing, on a storage device having at least one memory and which is connected with the server, for each respective monitoring device of the plurality of monitoring devices, the respective metadata in association with the respective monitoring device;
providing access to the respective metadata received from each respective monitoring device of the plurality of monitoring devices, by at least one remote computing device;
receiving, at the server, from the at least one remote computing device, a message indicating a correction to the respective metadata received by a first monitoring device of the plurality of monitoring devices, the storage device including at least one memory configured to store data;
determining, with the server, based on the correction, an update for at least one of (i) a model, (ii) an algorithm, and (iii) a threshold that was used by the first monitoring device to determine the respective metadata based on the respective sensor data; and
transmitting, with the server, the update to the plurality of monitoring devices.

2. The method of claim 1 further comprising:
receiving, at the server, from a first monitoring device of the plurality of monitoring devices, the respective sensor data from which the respective metadata was determined;
storing, on the storage device, for the first monitoring device, the respective sensor data in association with the first monitoring device; and
providing access to the respective sensor data received from the first monitoring device, by the at least one remote computing device.

3. The method of claim 1, the storing further comprising:
storing, on the storage device, for each respective monitoring device of the plurality of monitoring devices, the respective metadata in association with at least one of (i) a unique identifier of the respective monitoring device and (ii) a unique identifier of the respective vehicle in which the respective monitoring device is installed.

4. The method of claim 1, the providing access further comprising:
receiving, at the server, from the at least one remote computing device, a request message that identifies at least one of (i) a first monitoring device of the plurality of monitoring devices and (ii) the respective vehicle in which the first monitoring device is installed; and
transmitting, with the server, to the at least one remote computing device, the respective metadata received from the first monitoring device.

5. The method of claim 1, the providing access further comprising:
providing access to the respective metadata received from each respective monitoring device of the plurality of monitoring devices via at least one of (i) a web interface and (ii) an application programming interface.

6. The method of claim 1 further comprising:
transmitting, with the server, an alert message to the at least one remote computing device in response to the respective metadata of a first monitoring device of the plurality of monitoring devices indicating that a first predetermined condition of the at least one predetermined condition of the respective vehicle has occurred.

7. The method of claim 6, wherein the alert message is an email message.

8. The method of claim 6, wherein the alert message identifies a time at which the first predetermined condition occurred.

9. The method of claim 1, wherein the correction includes an indication that the respective metadata was determined incorrectly.

10. The method of claim 1, wherein the correction includes a corrected value for the respective metadata.

11. The method of claim 1, wherein the at least one predetermined condition of the respective vehicle includes smoking of a passenger of the respective vehicle being detected within the vehicle.

12. The method of claim 1, wherein the at least one predetermined condition of the respective vehicle includes an odor being detected within vehicle.

13. The method of claim 1, wherein the at least one predetermined condition of the respective vehicle includes damage to the respective vehicle being detected.

14. The method of claim 1, wherein the at least one predetermined condition of the respective vehicle includes a collision of the respective vehicle being detected.

15. The method of claim 1, wherein the at least one predetermined condition of the respective vehicle includes uncleanliness of a cabin of the respective vehicle being detected.

16. The method of claim 1, wherein the at least one predetermined condition of the respective vehicle includes an object left behind by a passenger being detected.

17. A system for managing data of a vehicle monitoring system, the server comprising:
a transceiver configured to communicate with a plurality of monitoring devices of the vehicle monitoring system, each monitoring device of the plurality of monitoring devices being installed in a respective vehicle and having at least one sensor configured to capture respective sensor data;
a storage device having at least one memory configured to store data received from the plurality of monitoring devices; and a processor operably connected to the transceiver and the storage device, the processor configured to:
- operate the transceiver to receive, from each respective monitoring device of the plurality of monitoring devices, respective metadata indicating whether at least one predetermined condition of the respective vehicle has occurred, the respective metadata being determined by the respective monitoring device based on the respective sensor data;
- operate the storage device to store, for each respective monitoring device of the plurality of monitoring devices, the respective metadata in association with the respective monitoring device;
- operate the transceiver and the storage device to provide access to the respective metadata received from each respective monitoring device of the plurality of monitoring devices, by at least one remote computing device;
- operate the transceiver to receive, from the at least one remote computing device, a message indicating a correction to the respective metadata received by a first monitoring device of the plurality of monitoring devices;
- determine, based on the correction, an update for at least one of (i) a model, (ii) an algorithm, and (iii) a threshold that was used by the first monitoring device to determine the respective metadata based on the respective sensor data; and
- operate the transceiver to transmit the update to the plurality of monitoring devices.

18. A non-transitory computer-readable medium for managing data of a vehicle monitoring system, the vehicle monitoring system having a plurality of monitoring devices, each monitoring device of the plurality of monitoring devices being installed in a respective vehicle and having at least one sensor configured to capture respective sensor data, the computer-readable medium storing program instructions that, when executed by a processor, cause the processor to:
- operate a transceiver to receive, from each respective monitoring device of the plurality of monitoring devices, respective metadata indicating whether at least one predetermined condition of the respective vehicle has occurred, the respective metadata being determined by the respective monitoring device based on the respective sensor data;
- operate a storage device to store, for each respective monitoring device of the plurality of monitoring devices, the respective metadata in association with the respective monitoring device the storage device including at least one memory;
- operate the transceiver and the storage device to provide access to the respective metadata received from each respective monitoring device of the plurality of monitoring devices, by at least one remote computing device;
- operate the transceiver to receive, from the at least one remote computing device, a message indicating a correction to the respective metadata received by a first monitoring device of the plurality of monitoring devices;
- determine, based on the correction, an update for at least one of (i) a model, (ii) an algorithm, and (iii) a threshold that was used by the first monitoring device to determine the respective metadata based on the respective sensor data; and
- operate the transceiver to transmit the update to the plurality of monitoring devices.

* * * * *

UNITED STATES PATENT AND TRADEMARK OFFICE
CERTIFICATE OF CORRECTION

| | | |
|---|---|---|
| PATENT NO. | : 11,875,617 B2 | Page 1 of 1 |
| APPLICATION NO. | : 17/116142 | |
| DATED | : January 16, 2024 | |
| INVENTOR(S) | : Ventimiglia et al. | |

It is certified that error appears in the above-identified patent and that said Letters Patent is hereby corrected as shown below:

On the Title Page

Under Item (56) References Cited, under heading "U.S. PATENT DOCUMENTS", in Line 1: "3,954,204 A 5/1976 Becker at al." should read --8,954,204 B2 2/2015 Everhart et al.--.

In the Claims

In Claim 18, at Column 22, Line 15: "monitoring device the storage device" should read --monitoring device, the storage device--.

Signed and Sealed this
Eleventh Day of June, 2024

Katherine Kelly Vidal
*Director of the United States Patent and Trademark Office*